(12) United States Patent
Sinz

(10) Patent No.: US 9,567,167 B2
(45) Date of Patent: Feb. 14, 2017

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Achim Sinz, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/724,035

(22) Filed: May 28, 2015

(65) Prior Publication Data

US 2015/0360876 A1    Dec. 17, 2015

(30) Foreign Application Priority Data

Jun. 17, 2014 (EP) ................................... 14172849

(51) Int. Cl.
| G08B 21/00 | (2006.01) |
| B65G 54/02 | (2006.01) |
| G01N 35/04 | (2006.01) |
| G01N 35/00 | (2006.01) |

(52) U.S. Cl.
CPC ......... *B65G 54/02* (2013.01); *G01N 35/00584* (2013.01); *G01N 35/04* (2013.01); *B65G 2207/20* (2013.01); *G01N 2035/0406* (2013.01); *G01N 2035/0477* (2013.01)

(58) Field of Classification Search
CPC G01N 35/02; G01N 35/04; G01N 2035/0477; B65G 54/02; B01L 9/06

USPC ........... 340/690; 198/619, 465.1; 422/63, 65
See application file for complete search history.

(56) References Cited

U.S. PATENT DOCUMENTS

| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grechsch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |

(Continued)

FOREIGN PATENT DOCUMENTS

| CN | 201045617 Y | 4/2008 |
| CN | 102109530 A | 6/2011 |

(Continued)

*Primary Examiner* — John A Tweel, Jr.
(74) *Attorney, Agent, or Firm* — Roche Diagnostics Operations, Inc.

(57) ABSTRACT

A laboratory sample distribution system comprising a number of sample container carriers moving on a transport plane is presented. The system further comprises an earthquake detection device in order to minimize influences on operation of the system by an earthquake. A laboratory automation system comprising such a laboratory sample distribution system is also presented.

10 Claims, 1 Drawing Sheet

(56) References Cited

U.S. PATENT DOCUMENTS

| | | |
|---|---|---|
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,428,957 B2 | 9/2008 | Schaefer |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,281,888 B2 | 10/2012 | Bergmann |
| 8,796,186 B2 | 8/2014 | Shirazi |
| 9,187,268 B2 * | 11/2015 | Denninger ............. B65G 54/02 |
| 9,211,543 B2 | 12/2015 | Ohga et al. |
| 9,239,335 B2 * | 1/2016 | Heise ................... B65F 54/02 |
| 2002/0009391 A1 | 1/2002 | Marquiss et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2008/0012511 A1 | 1/2008 | Ono |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0255529 A1 | 10/2010 | Cocola et al. |
| 2010/0312379 A1 | 12/2010 | Pedrazzini |
| 2011/0050213 A1 | 3/2011 | Furukawa |
| 2011/0172128 A1 | 7/2011 | Davies et al. |
| 2011/0186406 A1 | 8/2011 | Kraus |
| 2011/0287447 A1 | 11/2011 | Norderhaug et al. |
| 2012/0037696 A1 | 2/2012 | Lavi |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2014/0234978 A1 | 8/2014 | Heise et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 * | 12/2015 | Sinz ....................... B65G 54/02 198/619 |
| 2015/0360878 A1 | 12/2015 | Denninger et al. |
| 2016/0003859 A1 * | 1/2016 | Wenczel ................ G01N 35/04 422/561 |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 * | 3/2016 | Riether .................. G01N 35/04 422/65 |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski |
| 2016/0341750 A1 | 11/2016 | Sinz et al. |
| 2016/0341751 A1 | 11/2016 | Huber et al. |

FOREIGN PATENT DOCUMENTS

| | | |
|---|---|---|
| DE | 3909786 A1 | 9/1990 |
| DE | 102011090044 A1 | 7/2013 |
| EP | 0601213 A1 | 6/1994 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2502675 A1 | 9/2012 |
| EP | 2887071 A1 | 6/2015 |
| GB | 2165515 A | 4/1966 |
| JP | S56-147209 A | 11/1981 |
| JP | 60-223481 A | 11/1985 |
| JP | 61-081323 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 01-266860 A | 10/1989 |
| JP | H02-87903 A | 3/1990 |
| JP | 3-112393 A | 5/1991 |
| JP | 03-192013 A | 8/1991 |
| JP | H05-69350 A | 3/1993 |
| JP | H05-180847 A | 7/1993 |
| JP | 06-026808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H11-083865 A | 3/1999 |
| JP | H11-264828 A | 9/1999 |
| JP | H11-304812 A | 11/1999 |
| JP | H11-326336 A | 11/1999 |

(56) References Cited

FOREIGN PATENT DOCUMENTS

| | | |
|---|---|---|
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-062188 A | 3/2009 |
| JP | 2009-145188 A | 7/2009 |
| JP | 2009-300402 A | 12/2009 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 03/042048 A1 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2014/059134 A1 | 4/2014 |
| WO | 2014/071214 Z1 | 5/2014 |

\* cited by examiner

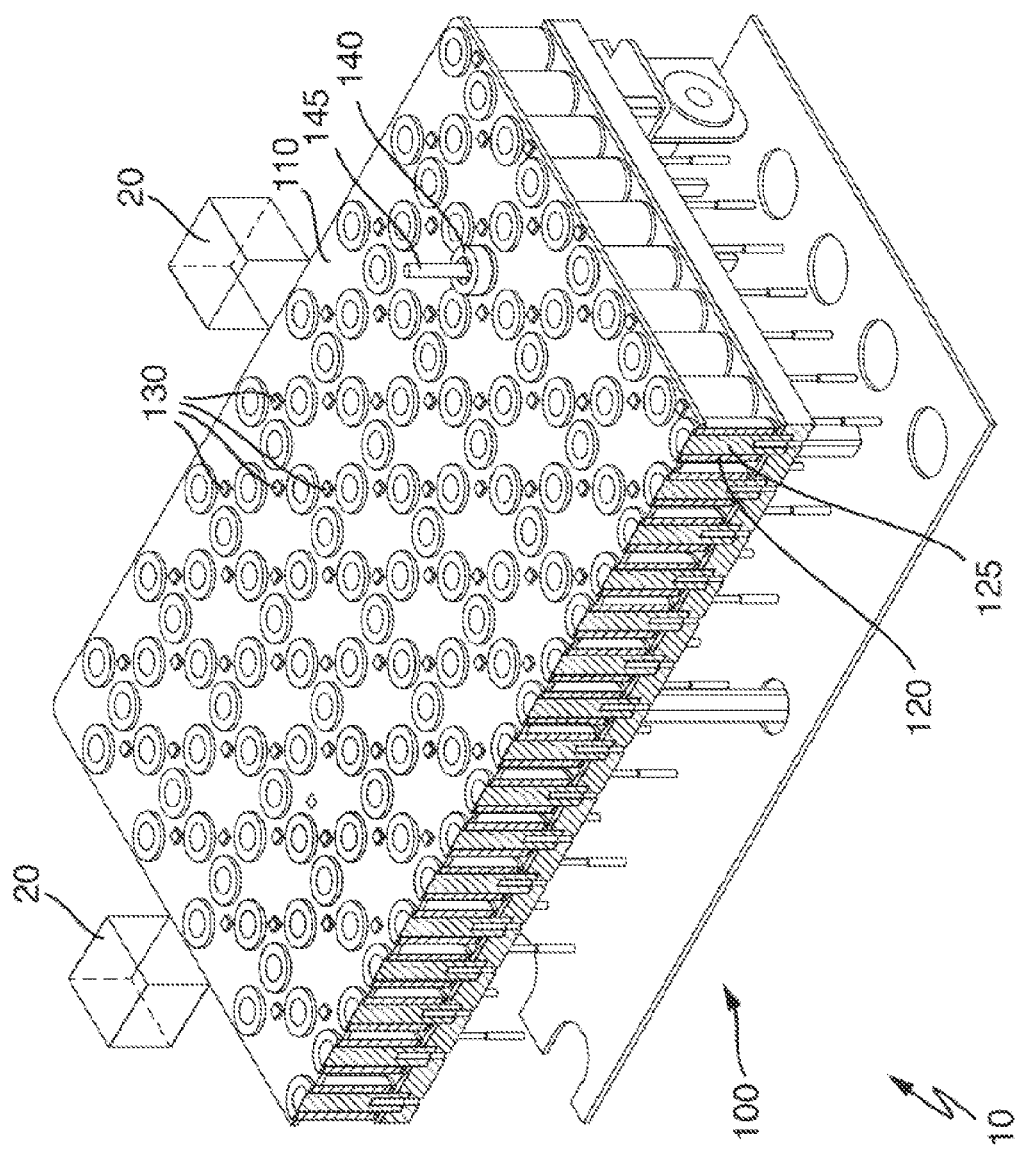

LABORATORY SAMPLE DISTRIBUTION SYSTEM AND LABORATORY AUTOMATION SYSTEM

CROSS-REFERENCE TO RELATED APPLICATIONS

This application claims priority to EP 14172849.3, filed Jun. 17, 2014, which is hereby incorporated by reference.

BACKGROUND

The present disclosure generally relates to a laboratory sample distribution system and a laboratory automation system.

Known laboratory sample distribution systems are typically used in laboratory automation systems in order to transport samples contained in sample containers between different laboratory stations.

There is a need for laboratory sample distribution systems and laboratory automation systems having improved resilience during an earthquake when compared to known laboratory sample distribution systems.

SUMMARY

According to the present disclosure, a laboratory sample distribution system is presented. The system can comprise a plurality of sample container carriers to carry one or more sample containers. Each sample container carrier can comprise at least one magnetically active device. The system can further comprise a transport plane to support the sample container carriers and a plurality of electro-magnetic actuators stationary arranged below the transport plane. The electro-magnetic actuators can move a sample container carrier on top of the transport plane by applying a magnetic force to the sample container carrier. The system can comprise a control device to control the movement of the sample container carriers on top of the transport plane by driving the electro-magnetic actuators such that the sample container carriers move along corresponding transport paths and an earthquake detection device communicatively coupled to the control device and configured to detect occurrence of an earthquake and to report a detected earthquake to the control device.

Accordingly, it is a feature of the embodiments of the present disclosure to provide for laboratory sample distribution systems and laboratory automation systems having improved resilience during an earthquake when compared to known laboratory sample distribution systems. Other features of the embodiments of the present disclosure will be apparent in light of the description of the disclosure embodied herein.

BRIEF DESCRIPTION OF THE SEVERAL VIEWS OF THE DRAWING

The following detailed description of specific embodiments of the present disclosure can be best understood when read in conjunction with the following drawing, where like structure is indicated with like reference numerals and in which:

FIG. 1 illustrates a laboratory automation system comprising a laboratory sample distribution system according to an embodiment of the present disclosure.

DETAILED DESCRIPTION

In the following detailed description of the embodiments, reference is made to the accompanying drawing that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system comprising a plurality of sample container carriers is presented. The sample container carriers can carry one or more sample containers. Each sample container carrier can comprise at least one magnetically active device. The magnetically active device may be a permanent magnet, an electromagnet and/or any magnetically soft material. The laboratory sample distribution system can further comprise a transport plane to support or carry the sample container carriers.

The laboratory sample distribution system can further comprise a plurality of electro-magnetic actuators. The electro-magnetic actuators can stationary be arranged below the transport plane and can move a sample container carrier on top of the transport plane by applying a magnetic force to the sample container carrier.

The laboratory sample distribution can system can further comprise a control device. The control device can control the movement of the sample container carriers on top of the transport plane by driving the electro-magnetic actuators such that the sample container carriers can move simultaneously along corresponding specific transport paths.

The laboratory sample distribution system can further comprise an earthquake detection device communicatively coupled to the control device to detect an occurrence of an earthquake and to report a detected earthquake to the control device.

The laboratory sample distribution system can detect an earthquake and can initiate counter measures preventing or reducing negative effects caused by the earthquake. In the case of an earthquake, it can, for example, be prevented the laboratory sample distribution system from having to be manually restarted or that damage or (uncontrolled) misplacement to sample containers or samples to be caused.

The sample containers can typically be designed as tubes made of glass or transparent plastic and can typically have an opening at an upper end. The sample containers can be used to contain, store and transport samples such as blood samples or chemical samples.

The transport plane can also be denoted as transport surface. The transport plane can support the sample container carriers, which can also be denoted as carrying the sample container carriers.

The electro-magnetic actuators can typically be built as electromagnets having a solenoid surrounding a ferromagnetic core. These electro-magnetic actuators may be energized in order to provide for a magnetic field that can be used to move or drive the sample container carriers. For that purpose, the at least one magnetically active device in each sample container carrier may be a permanent magnet. Alternatively or additionally, an electromagnet can be used.

The control device can typically be a microprocessor, a microcontroller, a field programmable gate array, a standard computer, or a similar device. In a typical embodiment, the control device can comprise a processor and storage. Program code can be stored in the storage in order to control the behavior of the processor when the storage code is executed on the processor.

The sample container carriers can typically move in two dimensions on the transport plane. For that purpose, the electro-magnetic actuators may be arranged in two dimensions below the transport plane. The electro-magnetic actuators may be arranged in a grid or matrix having rows and columns along which the electro-magnetic actuators can be arranged.

According to an embodiment, the control device can be configured to energize, at the occurrence of an earthquake, the electro-magnetic actuators such that the electro-magnetic actuators can exert, cause, and/or apply an attractive magnetic force on sample container carriers positioned above a respective electro-magnetic actuator. Typically, each electro-magnetic actuator can exert an attractive magnetic force on a sample container carrier positioned above it. Thus, the sample container carriers can be secured and fixed at a respective position where the sample container carrier is located at the occurrence of the earthquake. Further movement of the sample container carriers can be prevented, thus reducing the risk of tilting and/or movement on unintentional transport paths.

According to an embodiment, the control device can be configured to stop movement of all sample container carriers on the transport surface at occurrence of an earthquake. Thus, the current distribution of sample container carriers just before the earthquake can be maintained during the earthquake for further operation of the laboratory sample distribution system after end of the earthquake.

According to an embodiment, the control device can be configured to energize, at the occurrence of an earthquake, the electro-magnetic actuators such that the attractive magnetic force can be exerted on sample container carriers positioned above is larger than a magnetic force used to move the sample container carriers on top of the transport plane. Thus, a magnetic force can be exerted on the sample container carriers during the earthquake, preventing uncontrolled movement or tilting during the earthquake, can be maximized in order to also maximize the positive effects discussed above.

According to an embodiment, the control device can be configured to energize, at the occurrence of an earthquake, only those electro-magnetic actuators over which sample container carriers have been positioned before the earthquake. This can prevent uncontrolled movement of sample container carriers due to attractive forces exerted on them from electro-magnetic actuators positioned nearby, and it can furthermore save energy. Typically, the electro-magnetic actuators over which sample container carriers are positioned before and/or during the earthquake can exert an attractive force on the sample container carriers positioned above them.

If an earthquake lasts longer than a predetermined threshold duration, the electrical power provided to those electro-magnetic actuators over which sample container carriers are positioned may be reduced after the threshold duration, e.g. by pulsing a current and/or voltage provided to the coils of the electromagnetic actuators. The electrical power may be reduced to a power level that is sufficient to safely fix the container carriers at their current position.

According to an embodiment, the earthquake detection device can detect the end of an earthquake and report it to the control device. Thus, the control device may resume operation of the laboratory sample distribution system after the earthquake and may check if disturbances or other error conditions have occurred during the earthquake.

According to an embodiment, the control device can determine and save a first distribution of sample container carriers on the transport plane at the occurrence of an earthquake, to determine a second distribution of sample container carriers on the transport plane after the end of the earthquake, and to issue an error message, if the first distribution and the second distribution do not match. Thus, further operation of the laboratory sample distribution system can be prevented in case of a disturbance regarding distribution of sample container carriers during the earthquake. Thus, a potentially erroneous movement of sample container carriers can be prevented.

It should be noted that determining a distribution can be performed such that the control device can only have information regarding positions where a sample distribution carrier is located without having the ability to individually identify each sample container carrier. Such an embodiment can be easy to implement. However, a hypothetical switch of positions of two sample carriers may not be recognized. Alternatively, determining a distribution of sample container carriers can be performed such that the control device can have information regarding the specific position of each individual sample container carrier. Such an embodiment can, for example, be performed using RFID-tags or similar identification means. Thus, it can even be possible to detect switches of positions of two sample container carriers.

According to an embodiment, each sample container carrier can comprise an RFID-tag with which the control device can identify the sample containers carrier uniquely. Such an embodiment can, for example, be used in order to implement a determination of a distribution of sample container carriers, in which the control device can know about each specific position of the sample container carriers individually. The RFID-tag can also be used for further tasks, such as identifying a sample container carrier and/or a sample contained in a sample container carried by the sample container carrier at laboratory stations.

According to an embodiment, the control device can perform a redistribution operation after the end of the earthquake if an error message has been issued and can control the electro-magnetic actuators after the end of the earthquake such that sample container carriers can move further along corresponding transport paths over the transport plane if an error message has not been issued. The redistribution operation may be performed in order to move sample container carriers that may have been inadvertently moved due to the earthquake at different positions with respect to their respective positions before the earthquake back to the positions where they were located before the earthquake. Afterwards, normal operation of the laboratory sample distribution system can be resumed. In the case it is detected that a severe error has occurred during the earthquake, for example, a sample container carrier has been tilted, an error message may be issued to a user, instructing him to manually check the state of the laboratory sample distribution system and bring it in condition for further operation.

According to an embodiment, the earthquake detection device can comprise an accelerometer. The earthquake detection device may comprise a microelectromechanical sensor (MEMS). For example, an accelerometer comprised by the earthquake detection device can be made using microelectromechanical technology. This can provide for a reliable and small embodiment.

A laboratory automation system, comprising a number of a pre-analytical, analytical and/or post-analytical (laboratory) stations, and a laboratory sample distribution system to transport the sample container carriers and/or sample containers between the stations is presented. The stations may be arranged adjacent to the laboratory sample distribution system.

Pre-analytical stations may perform any kind of pre-processing of samples, sample containers and/or sample container carriers. Analytical stations may use a sample or part of the sample and a reagent to generate a measuring signal. The measuring signal can indicate if and in which concentration, if any, an analyte exists. Post-analytical stations may perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

Referring initially to FIG. 1, FIG. 1 shows a laboratory automation system 10 comprising a laboratory sample distribution system 100 and a number of pre-analytical, analytical and/or post-analytical stations 20 arranged adjacent to the laboratory sample distribution system 100. Self-evidently, more than the two stations 20 depicted in FIG. 1 may be comprised in the laboratory automation system 10.

The laboratory sample distribution system 100 can comprise a transport plane 110, under which a plurality of electro-magnetic actuators in the form of electromagnets 120 can be positioned. The electromagnets 120 can be implemented as solenoids having a solid ferromagnetic core 125.

Sample container carriers 140 can be positioned on the transport plane 110 and can be moved by the electromagnets 120. While it can be understood that a plurality of sample container carriers 140 can be positioned on the transport plane 110, due to simplicity only one sample container carrier 140 is depicted in FIG. 1. The sample container carrier 140 can hold a sample container 145, in which a sample to be analyzed can be contained.

The laboratory sample distribution system 100 can transport the sample container carriers 140 and/or the sample containers 145 between the laboratory stations 20. The laboratory stations 20 can be positioned adjacent to the transport plane 110 such that a sample container carrier 140 can be used to transport a sample contained in the sample container 145 to a respective laboratory station 20.

A plurality of Hall-sensors 130 can be arranged such that positions of respective sample container carriers 140 on the transport surface 110 can be detected.

The laboratory sample distribution system 100 can further comprise a control device 150. The control device 150 can control movement of the sample container carriers 140 on the transport plane by driving the electromagnets 120 such that the sample container carriers 140 can independently and simultaneously move along corresponding transport paths.

The control device 150 can be further electrically connected to an earthquake detection device 160. The earthquake detection device 160 can comprise a microelectromechanical acceleration sensor 162 and a computing unit 164. An earthquake can be detected by the microelectromechanical acceleration sensor 162. The computing unit 164 can permanently monitor capacitances in the acceleration sensor 162. A change of a capacitance can indicate that a cantilever in the acceleration sensor 162 has been moved, which can be an indication of an earthquake. Such acceleration sensors are per se known in the art.

In the case of the computing unit 164 detecting an earthquake, the computing unit 164 can report the occurrence of the earthquake to the control unit 150. The control unit 150 can then stop the movement of all sample container carriers 140, energize the electromagnets 120 over which sample container carriers 140 are positioned with a specifically high attractive force so as to hold them in place during the earthquake, and store the current position of the sample container carriers 140.

When the computing unit 164 detects that the earthquake has ended, it can report this fact to the control device 150. Then, the control device 150 can check if each sample container carrier 140 is still at the location at which it was before the earthquake. If this is the case, the control device 150 can resume operation of the laboratory sample distribution system 100 so that the sample container carriers 140 can move further along their respective transport paths.

In the case there is a difference in a position of a sample container carrier 140 before and after the earthquake, the control device 150 can issue an error message instructing a user to manually check the laboratory sample distribution system 100 and bring it into condition for further operation.

After the control device 150 has received an input from the user that the condition for further operation has been reached, the control device 150 can resume normal operation of the laboratory sample distribution system 100, i.e. all sample container carriers 140 can move further along their respective transport paths.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the system comprising:
   a plurality of sample container carriers to carry one or more sample containers, each sample container carrier comprising at least one magnetically active device;
   a transport plane to support the sample container carriers;
   a plurality of electro-magnetic actuators stationary arranged below the transport plane, the electro-magnetic actuators move a sample container carrier on top of the transport plane by applying a magnetic force to the sample container carrier;
   a control device to control the movement of the sample container carriers on top of the transport plane by driving the electro-magnetic actuators such that the sample container carriers move along corresponding transport paths; and
   an earthquake detection device communicatively coupled to the control device and configured to detect occurrence of an earthquake and to report a detected earthquake to the control device.

2. The laboratory sample distribution system according to claim 1, wherein, at an occurrence of an earthquake, the control device energizes the electro-magnetic actuators such that the electro-magnetic actuators exert an attractive magnetic force on sample container carriers positioned above.

3. The laboratory sample distribution system according to claim 2, wherein, at an occurrence of an earthquake, the control device energizes the electro-magnetic actuators such that the attractive magnetic force exerted on sample container carriers positioned above is larger than a magnetic force used to move the sample container carriers on top of the transport plane.

4. The laboratory sample distribution system according to claim 2, wherein, at an occurrence of an earthquake, the control device energizes only those electro-magnetic actuators over which sample container carriers have been positioned before the occurrence of the earthquake.

5. The laboratory sample distribution system according to claim 1, wherein the earthquake detection device detects the end of an earthquake and reports it to the control device.

6. The laboratory sample distribution system according to claim 5, wherein the control device:
- determines and saves a first distribution of sample container carriers on the transport plane at an occurrence of an earthquake,
- determines a second distribution of sample container carriers on the transport plane after the end of the earthquake, and
- issues an error message if the first distribution and the second distribution do not match.

7. The laboratory sample distribution system according to claim 6, wherein if an error message has been issued, the control device performs a redistribution operation, and if an error message has not been issued, the control device controls the electro-magnetic actuators after the end of the earthquake such that sample container carriers move further along corresponding transport paths over the transport plane.

8. The laboratory sample distribution system according to claim 1, wherein the earthquake detection device comprises an accelerometer.

9. The laboratory sample distribution system according to claim 1, wherein the earthquake detection device comprises a microelectromechanical sensor (MEMS).

10. A laboratory automation system, the system comprising:
- a plurality of pre-analytical, analytical and/or post-analytical stations; and
- a laboratory sample distribution system according to claim 1 to transport the sample container carriers and/or sample containers between the plurality of pre-analytical, analytical and/or post-analytical stations.

* * * * *